United States Patent [19]

Matsuoka et al.

[11] Patent Number: 4,871,834

[45] Date of Patent: Oct. 3, 1989

[54] MONOCLONAL ANTIBODIES SPECIFIC TO CEA

[76] Inventors: Yuji Matsuoka, 4-23-504, Minamisho 5-chome,, Sawara-ku, Fukuoka-shi, Fukuoka-ken; Masahide Kuroki, 45-1, Nanakuma 7-chome,, Jyonan-ku, Fukuoka-shi, Fukuoka-ken, both of Japan

[21] Appl. No.: 807,113

[22] Filed: Dec. 10, 1985

Related U.S. Application Data

[63] Continuation of Ser. No. 508,432, Jun. 27, 1983, abandoned.

[30] Foreign Application Priority Data

Jun. 30, 1982 [JP] Japan ................... 57-113780

[51] Int. Cl.[4] ................. A61K 39/00; G01N 33/577
[52] U.S. Cl. ......................... 530/387; 435/7; 435/68; 435/240.27; 424/9; 424/85.8; 424/88; 436/536; 436/539; 436/548; 436/813
[58] Field of Search .............. 435/7, 68, 240.27; 424/9, 85, 88; 436/548, 539, 536, 813; 530/387

[56] References Cited

U.S. PATENT DOCUMENTS

| | | |
|---|---|---|
| 4,140,753 | 2/1979 | Edgington et al. ............ 424/1.1 |
| 4,145,336 | 3/1979 | Edgington et al. ............ 424/1.1 |
| 4,180,499 | 12/1979 | Hansen ............ 260/11 R |
| 4,299,815 | 11/1981 | Hansen et al. ............ 436/540 |
| 4,331,647 | 5/1982 | Goldenberg ............ 424/1.1 |
| 4,348,376 | 9/1982 | Goldenberg ............ 424/1.1 |
| 4,349,528 | 9/1982 | Koprowski et al. ............ 424/1.1 |

OTHER PUBLICATIONS

Hedin, A. et al., Molecular Immunology, 19(12), 1641–1648, (1982).
Chemical Abstracts, I, 94:203339f, (1981).
Chemical Abstracts, II, 96:215704a, (1982).
Chemical Abstracts, III, 97:90148j, (1982).
Chemical Abstracts, IV, 98:32757s, (1983).
Kuroki et al.: Cancer Res., 41, 713–720, (1981).
Accolla et al.: Proc. Natl. Acad., Sci., U.S.A., 77, 563, (1980).
Mitchell, K. F., Cancer Immunol. Immunother., 10, 1, (1980).
Rogers, G. T. et al.: Br. J. Cancer, 43, 1, (1981).
Kupchik, H. Z. et al., Cancer Res., 41, 3306, (1981).
Kuroki et al., (see item No. 1 above).
Molecular Immunology, 19, 399, (1982).

*Primary Examiner*—Christine M. Nucker
*Attorney, Agent, or Firm*—Wolder, Gross & Yavner

[57] ABSTRACT

A process for producing monoclonal antibodies specific to carcinoembryonic antigen (CEA), comprising immunizing a mammal with a first CEA to produce cells capable of producing antibodies, collecting the cells from the mammal, fusing the collected cells with the cells of a line of myeloma of another mammal, selecting the thus-obtained hybridoma cells on the basis of their capacity to produce antibodies reactive with said first CEA, subjecting the thus-selected hybridoma cells to cloning, selecting the thus-obtained monoclones on the basis of the reactivities of monoclonal antibodies produced by them with at least one antigen selected from CEAs other than said first CEA and CEA-related antigens of normal adult human origin, culturing the thus-obtained monoclones and recovering the desired monoclonal antibodies from the spent culture. The selection may preferably be effected by radioimmunoassay using a marker antigen labelled with a radioactive substance. Monoclonal anti-CEA antibodies thus-produced have specific reactivity with the antigenic determinants of CEA molecules and thus may with advantage be used for various clinical applications and fundamental medical studies such as, for example, for determination of the concentration of CEA and CEA-related antigens.

12 Claims, No Drawings

MONOCLONAL ANTIBODIES SPECIFIC TO CEA

This application is a continuation of application Ser. No. 508,432, filed June 27, 1983.

BACKGROUND OF THE INVENTION

1. Field of the Invention

This invention relates to monoclonal antibodies specific to the antigenic determinants of carcinoembryonic antigen (hereinafter referred to as CEA), a process for producing such antibodies and the use of such antibodies.

2. Prior Art

CEA is a well known cancer-specific fetal antigen which is a kind of glycoprotein having a molecular weight of about 200,000±80,000 and a ratio of sugar to protein of about 1:1. The presence of CEA as a cancer-specific antigen in adenocarcinoma of human digestive tract was previously reported by Gold and Freedman [J. Exp. Med., 121, 439 (1965) and ibid., 122, 467 (1965)]. Although the significance of CEA for clinical uses such as, for example, a marker for detecting and treating human cancer by radioimmunoassay of CEA in blood as well as for various fundamental medical studies is widely recognised in the art, there are certain CEA-related normal antigens which make the cancer-specificity of CEA unclear because of their cross-reactivities with CEA. Examples of such CEA-related antigens include non-specific cross-reacting antigen (hereinafter referred to as NCA) which is a kind of glycoprotein having a molecular weight of about 80,000±30,000 and a sugar content of about 1:1 and which is found, for example, in human lung and spleen [Proc. Natl. Acad. Sci. USA., 69, 2492 (1972)] and normal faecal antigen (hereinafter referred to as NFA) which may further be classified into NFA-1, NFA-2 and normal faecal cross-reacting antigen (hereinafter referred to as f-NCA) as follows:

NFA-2 is a kind of glycoprotein having a molecular weight of about 200,000±50,000 and a ratio of sugar to protein of about 1:1. Its antigenic and physicochemical characteristics are very similar to those of CEA.

Both NFA-1 and NFCA appear to be decomposition products of NFA-2. NFA-1 is a low molecular weight antigen having a molecular weight of about 20,000 to 30,000 and a sugar content of about 13%, and NFCA is a kind of glycoprotein having a molecular weight of about 80,000±30,000.

In addition there is an antigen designated as faecal non-specific cross-reacting antigen (hereinafter referred to as f-NCA) in normal human faeces, of which the antigenic properties are substantially the same as those of the above-mentioned NCA. f-NCA is cross-reactive with CEA, NFCA and NFA-2 [Cancer Res., 41, 713–720 (1981)]. Thus, there are 4 types of CEA-related antigens of normal human faeces origin, which are of interest in this regard.

In order to use CEA as a cancer marker with better results, it is necessary to distinguish CEA clearly from such CEA-related antigens. For this purpose, it has hitherto been desired to provide an anti-CEA antibody having a definite specificity to the antigenic determinants of CEA. However, various polyclonal anti-CEA antibodies of the known types have commonly the disadvantage of unclear reaction specificity because such polyclonal anti-CEA antibodies comprise mixtures of various different antibodies which may react with almost all of the numerous antigenic determinants on the CEA molecule. For this purpose of overcoming such a difficulty, various attempts have hitherto been made to provide monoclonal anti-CEA antibodies because it has been believed in the art, for example, as follows:

(1) Monoclonal anti-CEA antibody may be specific to a sole antigenic determinant when prepared in conventional manner by fusing the cells and thus may have an uniform reactivity with antigen.

(2) It may be possible to produce a large amount of antibody having the desired uniformity by propagating such monoclones; and (3) It may be possible to provide many kinds of monoclones exhibiting a wide variety of specificity as in the case of polyclonal antibodies.

Thus, the production of monoclonal anti-CEA antibodies is disclosed, for example, by Accolla, R. S. et al, Proc. Natl. Acad. Sci. USA., 77, 563 (1980); Mitchell, K. F., Cancer Immunol. Immunother., 10, 1 (1980); Rogers, G. T. et al, Br. J. Cancer, 43, 1 (1981); Kupchik, H. Z. et al, Cancer Res., 41, 3306 (1981) etc. However, it has not yet been clarified which known monoclonal anti-CEA antibodies are specific to which antigenic determinants of the CEA molecule which has a very complicated antigenic structure.

Namely these reports disclosed in summary the following findings as to the reaction specificities of the monoclonal anti-CEA antibodies which they obtained:

(1) Accolla et al reported that the antibodies obtained from two hybridoma clones reacted very weakly with NGP (which is believed to be equivalent to NCA as hereinbefore described) and strongly with CEA and that the reactions of these two antibodies with CEA were not competitively inhibited in relation to each other indicated that they react with different antigenic determinants on the CEA molecule, respectively.

(2) Mitchell reported that a monoclonal anti-CEA antibody which he found reacted with CEA but not with NCA and that its reaction with CEA was not inhibited by a polyclonal goat anti-CEA antibody.

(3) Rogers et al merely reported that a monoclonal anti-CEA antibody reacted weakly with a CEA extracted from tumours but strongly reacted with another CEA extracted from patients' sera.

(4) Kupchik et al analysed the reaction specificty of only one preparation of monoclonal anti-CEA antibody which was produced by one clone out of 9 cloned hybridomas in comparison with that of a polyclonal goat anti-CEA antibody and reported that such monoclonal anti-CEA antibody reacted with a variant subpopulation of CEA molecules which were reactive with the polyclonal anti-CEA antibody.

No further clarification of the reaction specificities of these known monoclonal anti-CEA antibodies has been reported.

Meanwhile, we have found the presence of certain CEA-related antigens in normal adult faeces viz. NFA-1, NFA-2 and NFCA as hereinbefore described and have succeeded in isolating them [Japanese Patent Application as laid open to public inspection as Kokai Koho 46819/81; Cancer Res., 41, 713–720 (1981); and Molecular Immunology, Vol. 19, No. 3, pp. 399–406 (1982)] and moreover, as a result of investigating the antigenic structure of the CEA molecule using such CEA-related normal antigens, we have been able to classify many antigenic determinants on the CEA molecule, for example, into the following 5 types:

(1) Individual specific antigenic determinant:

Specifically present in a given CEA sample used as the immunising antigen and not present in any other human CEA sample.

(2) CEA-specific antigenic determinant:*

Commonly present in various human CEA samples and not in CEA-related normal antigens such as NFA and NCA. This determinant has the highest cancer-specificity.

(3) NFA-1 common antigenic determinant:*

Commonly present in CEA, NFA-2 and NFA-1. One of the main determinants on the CEA molecule.

(4) NFCA common antigenic determinant:*

Commonly present in CEA, NFA-2, and NFCA. One of the main determinants on the CEA molecule.

(5) NCA common antigenic determinant:*

Commonly present in CEA, NFA-2, NFCA and f-NCA. One of the widely distributed determinants of CEA and CEA-related antigens.

[* (2) to (5) c.f. Cancer Res.,41, 713–720 (1981)].

SUMMARY OF THE INVENTION

This invention is based upon the discovery that the above-mentioned CEA-related normal antigens may be used to select monoclones capable of producing monoclonal anti-CEA antibodies with respect to their reactivities with antigens.

This invention thus provides a process for producing monoclonal anti-CEA antibodies, monoclones for the preparation of such antibodies, and the use of such antibodies.

This invention provides a process for producing monoclonal antibodies specific to carcinoembryonic antigen (CEA), by immunising a mammal with a given CEA viz. a first CEA to produce cells capable of producing antibodies, collecting the cells from the mammal, fusing the collected cells with the cells of a line of a myeloma of another mammal, subjecting the thus-obtained hybridoma cells to cloning, culturing the thus-obtained monoclones and recovering the desired monoclonal antibodies from the spent culture, characterized in that said hybridoma cells are selected by using the first CEA as a marker, on the basis of their capacity to produce antibodies reactive with the marker antigen and that said monoclones obtained by cloning are selected, by using at least one marker antigen selected from second CEAs other than the first CEAs and CEA-related antigens originating from normal adult humans on the basis of the reactivities of monoclonal antibodies produced by them with said marker antigen(s).

According to a further feature of this invention, there are provided monoclonal antibodies produced by the above-described process as well as the monoclones themselves selected by the above-defined process.

DESCRIPTION OF SPECIFIC EMBODIMENTS:

Preferably, the CEA-related antigens are selected from NFA-1, NFA-2 and f-NCA originating from normal adult human faeces and the selection may be effected by radioimmunoassay using a marker labelled with a radio-active substance, as is well known in the art.

The monoclonal antibodies obtained from the monoclones of this invention exhibit uniform and specific reactivities with the desired antigenic determinants on the CEA molecule and thus may with advantage be used for various clinical applications such as, for example, for detecting and treating various human cancers as well as for various fundamental medical studies.

The monoclones which may be used for the purpose of this invention may be produced in conventional manner. Thus, for example as mammals to be immunised, smaller animals such as mice, rats, guinea pigs etc. and larger animals such as rabbits, goats, cattle, horses etc. may be used. They may be immunised in conventional manner. In the case where mice are used, for example, on each occasion, the animal may be immunised by injection (ip) using 20 μg of a given CEA sample viz said first CEA in a 0.2 ml emulsion with Freund's complete adjuvant and 5 weeks after this, with the same amount of the CEA in saline solution (0.2 ml) by intravenous injection. 3 days after the final immunisation, spleen and lymphnode cells may be collected from the animal in conventional manner. The antibody-producing cells thus collected may be mixed with suitable tumour cells (for example, P3-X63-Ag 8, 6, 5, 3 such as P3-X63-Ag8-U1; Sp 2/0-Ag 14; 210, RCY 3, Ag 1, 2, 3 and the like) in a ratio of $1 \times 10^8$ cells/ml: $1 \cong 2 \times 10^7$ cells/ml, that is, 5:1 to 10:1. The mixed cells may be fused in conventional manner, for example by using HVJ (Sendai virus) or PEG (polyethylene glycol). By selection using a HAT medium, normal cells are killed and the survivors represent the fused cells which are then selected on the basis of their capacity to produce antibodies reactive with the first CEA. The selected fused cells which are capable of producing anti-CEA antibody are subjected to cloning in conventional manner and the thus obtained monoclones are selected on the basis of the reactivity of antibody originating from the monoclones with CEA and CEA-related antigens as hereinbefore defined. The selection may preferably be effected by radioimmunoassay as known per se and in the hereinafter described example the selection was effected by Farr's ammonium sulfate precipitation method [Farr, R. S., J. Inf. Dis., 103, 239 (1958)]. Preferred examples of the CEA-related antigens originating from normal human faeces are NFA-1, NFA-2, and f-NCA having the abovementioned characteristics. The production of such CEA-related antigens is described in the reference hereinafter.

With reference to Table 1 showing the result of the selection effected in Example 1 described hereinafter, NFA-2, a CEA-related antigen originating from normal adult faeces is labelled with radioactive iodine and added to an aliquot of the spent culture of monoclone for immunoassay. In this manner, monoclones (clone A, about 10 clones in Example 1) capable of producing antibody A unreactive with NFA-2 and monoclones (clone B, about 200 clones in Example 1) capable of producing antibody B which is reactive with NFA-2 are separated from the monoclones (about 300 in Example 1) resulted from cloning. It should be appreciated that antibody A is reactive with human CEA and unreactive with CEA-related antigens originating from normal adult faeces.

TABLE 1

Selection of monoclones (cf. Example 1)

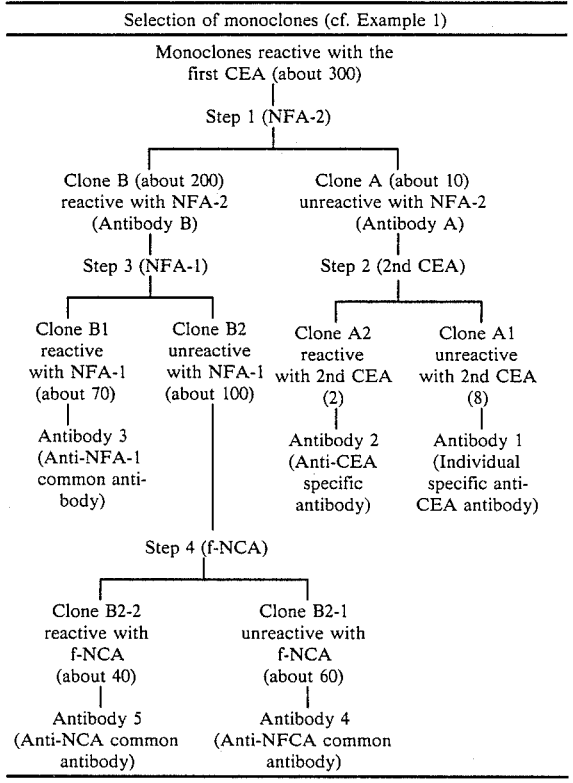

A similar radioimmunoassay may be effected by using at least one 2nd CEA (as hereinbefore defined; in Example 1, 4 CEA samples) other than the first CEA (as hereinbefore defined) used for immunizing the mammal. In this manner, it is possible to select clone A1 (8 clones in Example 1) capable of producing antibody 1 which is reactive with the first CEA and unreactive with the second CEA and clone A2 (2 clones in Example 1) capable of producing antibody 2 which is reactive with both the first and second CEAs.

A similar selection is effected by using NFA-1 to select clone B1 and B2 from clone B capable of producing antibody which is reactive with NFA-2. Clone B1 (about 70 in Example 1) are capable of producing antibody 3 which is reactive with NFA-1 and NFA-2, and clone B2 (about 100 in Example 1) are capable of producing antibody B2 which is reactive with NFA-2 and unreactive with NFA-1. Although NFA-1 has a smaller molecular weight, its antigenicity is so strong that about 70 clone B1 are selected in Example 1.

A similar immunoassay is effected by using f-NCA to select from clone B2 clone B2-1 (about 60 in Example 1) capable of producing antibody 4 which is unreactive with f-NCA and clone B2-2 (about 40 in Example 1) capable of producing antibody 5 which is reactive with f-NCA.

If desired, any antigen other than NFA-2 may be used at first to select the monoclones obtained by cloning. For example, by using NFA-1 at first, the monoclones may be selected with respect to the reactivities of their antibodies with NFA-1.

It has been found that the five types of monoclonal anti-CEA antibodies of this invention consist essentially, about 40% of IgM, about 50% of IgG and about 10% of IgA.

The anti-CEA antibodies of this invention may with advantage be used for various clinical applications and fundamental medical studies. Thus it will be appreciated in this regard that, for example, antibody 2 may be most advantageous for clinical uses and antibody 3 may be valuable for measuring the CEA concentration in blood. Moreover, monoclones of this invention may be propagated on an industrial scale in conventional manner.

The utilization of the anti-CEA antibodies of this invention may vary with differing antigenic specificities and expected uses of respective antibodies, although typical uses are exemplified as follows:

(1) Histological determination:

A cell sample (for example, cell suspension, smeared cells, sliced tissue and the like) is treated with an anti-CEA antibody of this invention at 37° C. for 30 minutes and washed well with saline solution. The sample is then treated with a solution of antimouse immunoglobulin labelled with a fluorescent pigment such as, for example, tetramethylrhodamine isocyanate, fluorescein isothiocyanate and the like at 37° C. for 30 minutes. The cells positive to the fluorescent pigment are determined by using a fluorescent microscope. If desired, it is possible to use, for example, the enzyme labelled antibody method using peroxidase coupled with antimouse immunoglobulin instead of the fluorescent pigment.

(2) Determination of the CEA concentration in blood:

The concentration of CEA in blood may be determined accurately by using the monoclonal antibodies of this invention, for example, by Farr's ammonium sulfate precipitation method, two antibodies method using antimouse immunoglobulin, Z gel method using zirconium gel, solid phase antibody sandwich method and the like, as exemplified in the following.

2-1. The two antibodies method using anti-mouse immunoglobulin may be effected, for example, in the following manner.

A sample of human serum (50 μl) is put into a plastic tube [Eiken tube No. 1, commercially available from Eiken Kagaku K.K., Japan; diameter 9.8 mm; length 8 cm] and 0.1M acetate buffer solution containing 0.5% B.S.A. (pH=6.0; 200 μl) is added. Normal mouse serum diluted (×50) with 0.1M acetate buffer solution [pH=6.0] is used to prepare a suitably diluted solution (50 μl) of a monoclonal anti-CEA antibody of this invention. The antibody solution is put into the plastic tube to effect reaction at 37° C. for 30 minutes and then a suitable sample of CEA, prepared by the method of hereinafter described Reference 1 (1.5 ng) labelled with $^{125}I$ and dissolved in a similar acetate buffer solution (50 μl), is added to effect another reaction at 37° C. for one hour. To the reaction mixture, a rabbit or goat anti-mouse immunoglobulin serum (100 μl) containing an anti-mouse immunoglobulin antibody in an amount sufficient to precipitate the immunoglobulin in the diluted normal mouse serum (x 50; 50 μl) is added and allowed to react at 4° C. overnight. The resultant precipitate is collected by centrifugation (3000 r.p.m./30 min.), washed with 0.9% saline solution and the radioactivity of the precipitate is measured by a gamma counter.

CEA solutions [each containing CEA sample other than that used for immunizing the mammal at a concentration of from 1 ng/ml to 50 ng/ml in 0.1M acetate buffer solution containing bovine gammaglobulin (1.2%) and BSA (0.5%); pH=6.0] are treated in a similar manner to that applied to the serum sample to prepare a standard calibration curve. The CEA concentration in blood may be determined from the value found in the test serum sample.

In general, it is not easy to specify the standard concentration of CEA in blood because such a concentration usually varies with differing types of anti-CEA antibodies used for determination. However, it is preferred to evaluate a concentration of more than 2-fold the standard deviation (S.D.) beyond the normal value as being unsound in order to detect malignant tumours.

2-2 The solid phase antibody sandwich method is exemplified as follows

As a solid phase primary antibody, a suitable monoclonal CEA-specific antibody of this invention may with advantage be used, which antibody is firstly adsorbed onto a plastic bead or tube and subsequently reacted with a CEA in the test sample. Then a further reaction is effected with a labelled secondary antibody viz. another anti-CEA antibody which is directed against the antigenic determinants not identical with the corresponding determinants in the primary antibody so that the labelled secondary antibody is bound to the CEA, depending upon the amount of the CEA in the test sample. A similar procedure may be repeated using predetermined amounts of the CEA to form a standard calibration curve. By the use of this curve the amount of the CEA in the test sample may be determined.

(1) Preparation of primary antibody:

The solid phase primary antibody may be prepared for example as follows.

The selection of the anti-CEA monoclonal antibody of this invntion used as the primary antibody depends upon various factors such as, for example, the purpose of the determination and the like, although antibody 3 as hereinbefore described may advantageously be used for overall purposes because this antibody is directed against the most important antigenic sites of the CEA molecule designated as the NFA-1 common antigenic determinants. For this purpose, it is preferred to select an antibody 3 having an affinity constant (Ka) of greater than $1 \times 10^9 M^{-1}$ from monoclonal antibodies identified as antibody 3 as hereinafter described. The selection may be effected in the following manner.

On each occasion, to a limited amount of the sample of antibody 3 (e.g. 10μg), an increasing amount up to 200 μg of a CEA labelled with $^{125}I$ in 0.01M borated-buffered saline (BBS) [pH 8.0; containing normal rabbit serum (1%) and $NaN_3$ (0.05%)] is added. The mixture is incubated at 37° C. for 18 hours and a 75% saturated ammonium sulfate solution (400 μl) is added to the mixture which is then allowed to stand at 4° C. for one hour, followed by centrifugation (1800 G/30 min.) to remove the supernatant. The precipitate thus-obtained is washed with a half-saturated ammonium sulfate. An aliquot (200 μl) of the supernatant and the precipitate are counted using a gamma counter. A similar procedure is repeated and the results are plotted as 1/bound CEA against 1/free CEA to calculate Ka in conventional manner [Steward M, W, and Petty R, E, Immunol., 22,747(1972)].

The thus-obtained sample of anti-CEA having a high affinity is diluted (for example x 500) with a phosphate buffer solution [0.001M; pH 6.0; containing sodium lauryl sulfate (0.01%) and EDTA (0.05%)] to give an antibody concentration of about 5 to 10 μg/ml and used for coating the plastic bead or tube.

As a solid phase matrix, various tubes and beads of plastics material may be used. For example, polystyrene beads (diameter about 6 mm; commercially available from Precision Plastic Ball Co., U.S.A.) are well washed and dipped into the above-mentioned solution of monoclonal antibody 3 at ambient temperature overnight. Then, the beads are washed twice with distilled water, treated with a 0.001M glycine-hydrochloric acid buffer solution (pH 2.3), washed twice with distilled water, dipped into a 0.1M phosphate buffer solution containing 0.5M sodium chloride and 0.5% bovine serum albumin (BSA) for 3 hours and dried in vacuo for preservation in a cool place.

(2) Preparation of secondary antibody:

Depending upon the types of antibodies used as the labelled secondary antibody, the results may vary significantly. For example, by the use of antibody 2 as hereinafter described, it is possible to prepare a determination system which exhibits a high cancer-specificity and which is reactive with CEA originating from cancer tissue alone and is not reactive with CEA-related antigens such as NFA and NCA, whilst the use of antibody 5 may result in a system which is capable of determining CEA and CEA-related antigens except NFA-1, as is apparent from Table 2 as hereinafter indicated. Among various antibodies identified as antibody 3, one reacting with the same antigenic determinanats as the antigenic determinants reactive with the primary antibody should not be used as the secondary antibody, whilst another reacting with different antigenic determinants from those for the primary antibody can be used as the second antibody. The system exemplified in the following may exhibit the highest cancer-specificity owing to the use of antibody 2.

In a similar manner to that described above, among various monoclonal anti-CEA antibodies identified as antibody 2, one having a high affinity constant with CEA viz. having a Ka of greater than $1 \times 10^9 M^{-1}$ is selected. A CEA adsorbent as described in Reference 2 hereinafter [obtained by combining 10 mg of CEA with 1 g (dry weight) of Sepharose 4B (Pharmacia Fine Chemicals AB., Sweden)] is used to specifically purify the antibody 2 by the method described in Reference 2 hereinafter. The thus-obtained antibody sample is labelled with $^{125}I$ in conventional manner [e.g. the chloramine T method: Hunter and Greenwood, 1962, Nature (London) 194, 495] to prepare labelled antibody having a radioactivity of about 5 nCi/ng.

(4) Radioimmunoassay:

As test sample, human serum or plasma (50 μl) is put into a plastic test tube [for example, Eiken tube, $9.8 \times 80$ mm; commercially available from Eiken Kagaku K.K., Japan), to which a 0.1M acetate buffer solution [pH 6.0; 200 μl; containing BSA (0.5 %)] is added. An above-mentioned plastic bead combined with antibody 3 is put into this test tube which is then incubated at ambient temperature for 4 hours with rotation to effect reaction. After this, the reaction solution is sucked out, washed once with a 0.9% sodium chloride solution (1 ml) and added to a solution (200 μl) of secondary antibody labelled with $^{125}I$ [prepared by diluting to 600 nCi/ml with a 0.05M tris-HCl buffer solution containing 1% BSA]. The test tube is rotated at ambient temperature for 24 hours to effect reaction. After completion of the reaction, the reaction solution is sucked out and the bead is washed twice with 0.9% sodium chloride solution (each 1 ml). A gamma counter is used to determine the radioactivity of the bead.

For the preparation of a standard calibration curve, standard solutions, each consisting of a 0.1M acetate buffer solution [pH 6.0]; containing bovine gamma-globulin (1.2%), BSA (0.5%) and purified CEA (1 ng/ml, 3 ng/ml, 10 ng/ml, 30 ng/ml, or 100 ng/ml) are used. On each occasion, the standard solution (50 μl) is treated in a similar manner to that applied to the above-mentioned test sample to effect the reactions respectively with the antibody coated bead and with the radio-labelled secondary antibody. In this manner, the radioactivity of each standard solution [B cpm] is obtained, from which the corresponding value B' of the control solution not containing CEA is calculated to obtain a value B-B'. The thus-obtained values B-B' and the corresponding CEA concentrations are plotted to give a standard calibration curve which may be used for calculating the CEA concentration in the test sample.

The reactivity of antibody 2 used as the labelled secondary antibody with normal human serum or plasma is usually rather weak. Furthermore it is, in general, not easy to specify the normal CEA concentration because the average value may vary considerably depending on properties such as for example the affinity constant of the anti-CEA antibody used for determination. However, it is preferred in practice to evaluate a concentration of more than 2 folds of the standard deviation (S.D.) beyond the normal average value as being unsound in order to detect malignant tumours.

2-3 Thus, according to a further feature of this invention, there is provided a process for determining the concentration of carcinoembryonic antigens and carcinoembryonic antigen-related antigens, which comprises using a monoclonal antibody of this invention as a marker antibody labelled with a radioactive substance. By this process, it is possible to determine the concentration of the antigen or antigens more exactly than has hitherto been possible using conventional polyclonal and monoclonal anti-CEA antibodies.

In addition to the detection and treatment of cancer, the monoclonal anti-CEA antibodies of this invention may be used, for example, for clarification of the increase in the CEA production in accordance with the malignant transformation of the cells viz. a kind of reversion of the gene expression toward the fetal period and investigation of the biological activity and molecular structure of CEA.

The following non-limiting examples illustrate the invention.

In the examples, Farr's method of radioimmunoassay was effected in the following manner:

A CEA sample of (5–10 ng; 50 μl) labelled with $^{125}$I and a supernatant of the cultured monoclone (50 μl) were put into each well of a microtitre plate having 96 wells and well mixed. After incubating at 37° C. for one hour, a saturated ammonium sulfate solution (100 μl) was added to the mixture for further incubation at 37° C. for one hour. Then, the reaction mixture was centrifuged (2000 r.p.m./30 min.) to separate the supernatant, of which 100 μl was used for measuring the radioactivity using a gamma counter. From the amount of radioactive CEA co-precipitated with the antibody the fused cells capable of producing monoclonal anti-CEA antibody were identified.

EXAMPLE 1

Two mice (BALB/c; SPF; 5 weeks old) were used as test animals. On each occasion, the animal was immunized by abdominal injection of a sample of CEA (20 μg; prepared by the method of hereinafter described Reference 1) emulsified with Freund's complete adjuvant (0.2 ml). 5 weeks after this, the same amount of the CEA (20 μg in 0.2 ml of a saline solution) was intravenously injected into each animal. 3 days after this, the animals were sacrificed and lymphoid cells were collected from the spleen and lymph node of each animal. $1 \times 10^8$ lymphoid cells were mixed with $1 \times 10^7$ azaguanine-resistant lined myeloma cells originating from mouse myeloma [P3-X63-Ag8-U1 myeloma; Yelton D. E. et al, Curr. Top. Microbiol, Immunol., 81, 1 (1978)]. 1 ml of 45% (v/v) of polyethylene glycol 4000 [Sigma Chemical Co., U.S.A.] was dropwise added to the mixture, followed by incubation at 37° C. for 7 minutes. Then, D-MEM (15 ml; Nissui Seiyaku K.K., Japan) was dropwise added to the mixture to dilute the polyethylene glycol. The fused cells were washed with D-MEM (30 ml) and suspended in D-MEM [100 ml; containing 10% fetal calf serum (FCS; Gibco., U.S.A.], penicillin (100 unit/ml) and gentamicin (50 μg/ml)]. The cell suspension (1 ml aliquots) was distributed in 96 wells of microtitre plates, each having 24 wells, and incubated at 37° C. overnight in a $CO_2$ atmosphere. Next day, 1 ml of a HAT medium [D-MEM containing $4 \times 10^{-7}$M aminopterin, $1.6 \times 10^{-5}$M thymidine and $1 \times 10^{-4}$M hypoxanthine; pH=7.0) was added to each well, and then ½ of the medium was replaced by a fresh HAT medium with 2 day intervals. On the 11th day, ½ of the medium was replaced by HT medium (similar to HAT medium without aminopterin). Then, every 2 days, ½ of the medium was replaced by D-MEM containing 10% FCS. Growth of the fused cells was observed in nearly all wells (more than 98%). The supernatant of the culture was collected from each well and the screening of hybridoma was effected by Farr's ammonium sulfate precipitation method using the first CEA as hereinbefore defined to confirm the presence of anti-CEA antibodies in about 20 wells. The thus-obtained fused cells capable of producing anti-CEA antibodies were subjected to cloning by the limiting dilution method [by Watanabe et al] in the following manner. On each occasion, the fused cell culture was diluted with D-MEM containing 10% FCS to give a concentration of 3 cells/ml, of which 0.2 ml was put into each well of a microtitre plate. After culturing at 37° C. for 2 weeks by using D-MEM containing the X-irradiated thymic cells of young BALB/c mice (about $5 \times 10^6$ cells/ml), the cells capable of propagating in the wells were identified as monoclonal fused cells which were further subjected to the limiting dilution method to ensure the productivity of monoclones.

Farr's method as hereinbefore described was used to confirm whether or not the reaction of the supernatant of each culture of the thus-obtained monoclones with the first CEA was sufficient to obtain monoclones capable of producing more than about 10 ng/ml of anti-CEA antibodies. Although a CEA sample obtained by the method of hereinafter described Reference 1 was used as the first CEA in Example 1, if desired it is possible to use another suitable CEA for such a purpose.

Usually, about 20–30 monoclones of the desired type were obtainable by using two mice, and thus a similar procedure was repeated many times until about 300 monoclones were obtained. After this, the reactivities of the spent culture of the monoclones with samples of CEA, NFA-1, NFA-2 and f-NCA as hereinbefore described and labelled with radioactive iodine were respectively investigated, on each occasion, by using Farr's radioimmunoassay using ammonium sulfate. The results are hereinbefore described with reference to Table 1.

EXAMPLE 2

Antibodies 1-5 obtained in Example 1 (cf. Table 1) were further investigated by Farr's radioimmunoassay method using the first and second CEAs and normal related antigens of normal human faecal origin viz. NFA-1, NFA-2 and f-NCA because the selection steps shown in Table 1 were insufficient to completely clarify the reactivities of antibodies 1-5 with such antigens. The results are shown in Table 2 wherein "+" or "−" indicates the reactivity being positive or negative.

TABLE 2

Reactivities of monoclonal anti-CEA antibodies with CEA and CEA-related antigens:

| Antigen | Antibody 1 | 2 | 3 | 4 | 5 |
|---|---|---|---|---|---|
| Human CEAs | | | | | |
| First CEA* | + | + | + | + | + |
| Second CEA** | − | + | + | + | + |
| Normal related antigens | | | | | |
| NFA-1 | − | − | + | − | − |
| NFA-2 | − | − | + | + | + |
| f-NCA | − | − | − | − | + |

Notes:
*CEA used for immunizing the mammal.
**At least one CEA other than the first CEA From Table 2, the following specificities of the monoclonal anti-CEA antibodies of this invention are apparent:

(1) Antibodies 1-5 are reactive with the first CEA viz. the CEA sample used for immunizing the mammal.

(2) Antibody 1 is reactive with the first CEA alone. This antibody is of interest in detecting and treating individual cancer and represents an individual specific antibody.

(3) Antibody 2 is reactive with both the first and second CEA samples (in Example 1, 4 CEA samples respectively obtained from different patients were used as the second CEA), the unreactive with all CEA-related normal faecal antigens viz. NFA-1, NFA-2 and f-NCA. Antibody 2 represents an anti-CEA specific antibody and exhibits the highest cancer-specificity and may be used for overall purposes including various clinical applications (e.g. confirmative detection of cancer, carrier of radioactive or chemical agents toward the cancer tissues and the like) and fundamental medical studies.

(4) Antibody 3 is also valuable for practical purposes because this antibody is reactive with NFA-1 and NFA-2 in addition to the reactivity with the first and second CEAs. Moreover, the selection of the monoclone capable of producing antibody 3 is simpler than the selection of antibodies capable of producing other antibodies.

(5) Other antibodies i.e. 4 and 5 are also superior to conventional polyclonal anti-CEA antibodies with respect to their definite reactivity and uniformity.

EXAMPLE 3

30 mice were used as test animals. Fused cells (clones) were implanted into the abdominal cavity of each mouse (male or female) in the following manner.

On each occasion, pristan (0.5 ml) was administered into the abdominal cavity of BALB/c mice. 7-10 days after this, D-MEM (0.5 ml) containing the monoclonal hybridoma cells produced by the method of Example 1 (about $5 \times 10^6 - 10^7$ cells/ml) were abdominally given to the mouse. 7-10 days after this, a significantly large amount of ascites was found in the abdominal cavity, which was taken out by puncture. Then the ascites was collected 5 times at an interval of 2 days. Finally, the animal was killed and the blood was collected entirely. The volume of the collected ascites varied, depending upon the characteristics of the monoclones used and amounted to from 2 ml to 20 ml (about 10 ml on average). Also, the concentrations of the anti-CEA antibodies contained in the ascites and sera varied considerably, depending upon the characteristics of the monoclones and amounted to about 1 to 10 mg/ml. The weight of the antibodies obtained from the ascites and sera of respective animals also varied considerably and amounted to from about 2-3 mg to more than 100 mg per animal.

REFERENCES

In the following references, the concentration or evaporation of any protein solution by drying with air under pressure was effected in the following manner.

A solution to be concentrated was put into several cellophane tubes, for example, a solution (3 l) was put into 8-9 tubes [Visking Corpn., U.S.A.; 18/32; length 150 cm]. On each occasion, the tube was connected to a suitable conduit at the top. The conduit was connected to a suitable source of pressurized air such as, for example, an electric air pump. The tube was supported vertically and about 1/5 of the lower part of the tube was dipped into a vessel filled with desalted water or a suitable buffer solution. The remaining portion of the tube was exposed to wind supplied by an electric fan.

REFERENCE 1

Production of CEA sample:

[see Japanese Patent Application as laid open to public inspection as Sho-56-47762 (47762/81)]

The CEA sample used in this specification was prepared in the following manner unless otherwise specified.

A cancer tissue (120 g) collected from a metastatic liver tumour of colonic adenocarcinoma was ground down with addition of a physiological solution of sodium chloride (700 ml), followed by centrifugation (9000 r.p.m./40 min.) to result in a supernatant. To the supernatant (710 ml) was added a 60% perchloric acid solution (80 ml) to give a precipitate. The precipitate was removed from the supernatant by centrifugation (9000 r.p.m./40 min.). The thus-obtained supernatant was dialyzed with tap water overnight to remove perchloric acid and dialytic impurities completely. The residual solution was put into 3 cellophane tubes (Visking tube; 18/32; length 150 cm), followed by evaporation to give a concentrated solution (8 ml in total). A crude CEA solution was obtained by subjecting the concentrated solution to centrifugation (15000 r.p.m./30 min.) and treated as follows.

A column (2.6×171 cm) packed with a gel containing 4% agarose [Sepharose 4B, Pharmacia Fine Chemicals AB., Sweden] was washed with a sodium phosphate buffer solution [0.05M; pH=5.2] and charged with the crude CEA solution (7.5 ml). Elution was effected using a similar buffer solution to give fraction No. 4B-1 appearing in the same position as the void volume of the column and fractions 4B-2 to 4B-4 which appeared respectively at positions of 2.1, 2.5 and 2.7 folds of the void volume.

Fraction No. 4B-2 contained the major portion of CEA, which was collected, followed by evaporation to give a concentrated solution (3.5 ml).

A column (1.9×145 cm) packed with a gel containing 6% agarose [Sepharose 6B, Pharmacia Fine Chemicals AB., Sweden] was washed with a sodium phosphate buffer solution (0.05M; pH=5.2) and charged with the concentrated fraction No. 4B-2 (3.5 ml). Elution was effected using a similar buffer solution and an unsymmetrical peak was observed at the position 1.6 fold of the void volume of the column. The fraction appearing at the initial stage of the elution (Fraction No. 6B-1; about 20 ml) containing impurities having high molecular weight and the last portion of the eluate (Fraction No. 6B-3; about ⅓ of the eluate) containing NCA (non-specific cross-reacting antigen) were discarded. The middle portion (about ⅔ of the eluate; about 60 ml) was collected and concentrated by evaporation to obtain Fraction No. 6B-2 (3 ml).

A column (1.9×145 cm) packed with Sephadex G-200 [Pharmacia Fine Chemicals AB., Sweden] was washed with a similar sodium phosphate buffer solution and charged with Fraction 6B-2 (3 ml). Elution was effected using a similar buffer solution. At the position of about 1.2 folds of the void volume of the column, a symmetrical peak was observed. The eluate appearing in the middle three fourth of this peak (about 45 ml) was collected, followed by evaporation to give a concentrated solution, from which a purified CEA (50 mg) was recovered. The high purity of this substance was confirmed, for example, by immunoelectrophoresis. This substance is a kind of glycoprotein having a molecular weight of about $200,000 \pm 80,000$, a maximum absorption at 277 nm, a small shoulder at 283 nm in the ultraviolet spectrum, and a ratio of sugar to protein of about 1:1.

REFERENCE 2

[see Japanese Patent Application as laid open to public inspection as Kokai Koho 46819/81 Cancer Res., 41, 713, (1981) Molecular Immunol., 19, 399, (1982)]

Preparation of CEA-related antigens NFA-1, NFA-2 and f-NCA:

A normal faeces (250 g) from an adult was added to a 0.6M perchloric acid solution (2500 ml) and well mixed, followed by filtration using a gauze to remove insolubles such as food remnants.

Then the mixture was centrifuged (7000 r.p.m./30 min.) to give a supernatant which was dialysed with tap water overnight to remove perchloric acid and dialystic impurities completely. The residual solution was put into 9 cellophane tubes (Visking tube; 18/32 length 150 cm) and concentrated by evaporation to give an amount of 30 ml in total. A similar procedure was repeated 4 times to obtain a crude extracted solution (120 ml in total) from normal adult faeces.

This concentrated solution contained about 10 mg of the desired CEA-related antigens in total. To this solution was added an anti-CEA antibody adsorbent coupled with a specific anti-CEA antibody (as hereinafter described; 100 mg) and the reaction was effected at 4° C. for 24 hours. The adsorbent was recovered by filtration with sintered glass, and thoroughly washed with a cold borate buffered saline solution (0.01M borate buffer pH 8.0, 0.15M NaCl; hereinafter referred to as B.B.S) and eluted with a glycine-HCl buffer solution (0.175M; pH=2.3; 200 ml), followed by neutralizing with a glycine-NaOH buffer solution (1.0M; pH=9) to obtain a solution containing 9 mg (dry weight) of crude CEA-related antigens. The solution was concentrated by evaporation (as hereinbefore described) to give an amount of 1.2 ml, and transferred to a column (1.3×80 cm) packed with Sepharose 6B [Pharmacia Fine Chemicals AB., Sweden]. Elution was effected with a phosphate buffer solution [0.01M; pH 5.0; containing NaCl (0.15M)] and the eluate was divided into fractions (each 1 ml). The eluate in test tubes Nos. 60-75 [Fraction No. 1]and Nos. 81-95 [Fraction No. 2] were collected and combined respectively. Fraction No. 1 was concentrated to about 1 ml and transferred to a column packed with 100 ml of Sephadex G-200 (Pharmacia Fine Chemicals AB., Sweden). By eluting Fraction No. 1 with a similar phosphate buffer solution and dividing the eluate into equal fractions (each 1 ml), a purified NFA-2 was present in test tubes Nos. 30-40 which were collected and combined. The combined solutions may be used as a sample of NFA-2 after concentration. Thus-obtained NFA-2 was a kind of glycoprotein having a molecular weight of about $200,000 \pm 30,000$, a maximum absorption at 277 nm in the ultraviolet spectrum and a ratio of sugar to protein of about 1:1. The amino acid composition of the thus-obtained NFA-2 was very similar to that of CEA and the NH$_2$-terminal amino acid sequence of NFA-2 was identical to that of CEA through to at least position 11 [Cancer Res., 41, 713, (1981); Molecul. Immunol., 19, 399, (1982)].

Brown pigments were removed from Fraction No. 2 by diethylaminoethyl cellulose chromatography in a manner described in Cancer Res., 41, 713, (1981), and the remaining solution (100 ml) was added to an anti-NCA antibody adsorbent (as hereinafter described) (3.5 ml). The mixture was subjected to reaction at 4° C. for 2 days. The adsorbent was recovered and washed thoroughly, then eluted with glycine-HCl buffer solution (0.175M; pH 2.3; 20 ml) and neutralized with a glycine-NaOH buffer solution [1 M; pH=9.0]. The obtained solution was dialyzed against B.B.S. and concentrated by evaporation. This solution contained a purified NCA (dry weight 1 mg) which may be used for the purpose of this invention without further purification. The thus-obtained f-NCA was a kind of glycoprotein having a molecular weight of about $80,000 \pm 30,000$, a sugar content of about 20%, and an identical NH$_2$-terminal amino acid sequence to that of CEA through to at least position 20. The physicochemical properties of f-NCA were substantially the same as NCA obtained, for example, from lung or spleen.

The solution containing substances which had not been adsorbed onto the anti-NCA antibody adsorbent (as hereinafter described) was concentrated to 0.5 ml and treated in a similar manner to that described above using a column (1.3×43.4 cm) packed with Sephadex G-100 super fine [Pharmacia Fine Chemicals AB., Sweden]. Elution was effected with a similar phosphate buffered solution (0.01M, pH 5.0, 0.15M NaCl) and the eluate was divided into equal fraction (each 0.5 ml). The eluate in test tubes Nos. 45-55 (Fraction a) and 65-75 (Fraction b) were respectively collected and combined. Fractions a and b were rechromatographed respectively on the same column (1.3×43.4 cm) packed with Sephadex G-100 super fine. In this manner, from Fractions a and b, purified NFCA (dry weight 0.5 mg) and NFA-1 (dry weight 0.5 mg) were obtained respectively. They may be used for the purpose of this invention without further purification. The thus-obtained NFA-1 was a kind of glycoprotein having a molecular weight of about 20,000 to 30,000 and a sugar content of about 13%. The amino acid composition of NFA-1 was similar to that of CEA though slight but definite differences were observed in some amino acids such as phenylalanine, lysine and proline. The NH$_2$-terminal amino acid sequence of NFA-1 was, however, entirely different from that obtained for CEA, NFA-2 or NCA [Cancer Res., 41, 713, (1981); Molecul. Immunol., 19, 399, (1982)].

The anti-CEA antibody adsorbent and anti-NCA antibody adsorbent used herein were prepared in the following manner [see Cancer Res., 41, 713–720 (1981)].

A CEA sample prepared by the method of Reference 1 (10 mg in dry weight) was coupled with CNBR-Sepharose 4B (1 g dry gel) [Pharmacia Fine Chemicals AB., Sweden] in a conventional manner to obtain a CEA-adsorbent which was then reacted with an anti-CEA antiserum (50 ml) at 4° C. for 3 days. For the preparation of the antiserum, a suitable CEA may be used.

The CEA-adsorbent which bound anti-CEA antibody was recovered and well washed with cold B.B.S. until no protein appeared. Then, the adsorbent was eluted 5 times with glycine-HCl buffer solution (each 10 ml; 0.175M; pH 2.3). The eluted solutions were combined and neutralized with a glycine-NaOH buffer solution (1M; pH 9). Then the neutralized solution was dialyzed against B.B.S. at 4° C. overnight. The thus-obtained solution was concentrated to 10 ml; this contained specific polyclonal anti-CEA antibody (50 mg). The above-mentioned procedure was repeated twice to obtain 20 ml of the concentrated solution which contained 100 mg of specifically purified polyclonal anti-CEA antibody. The thus-obtained 100 mg of anti-CEA antibody was coupled with 10 g of CNBR-Sepharose 4B [Pharmacia Fine Chemicals AB., Sweden] in a conventional manner to obtain the desired anti-CEA antibody adsorbent coupled with 100 mg of specifically purified anti-CEA antibody.

The adsorbent of anti-NCA antibody coupled with Sepharose 4B may be produced in a similar manner to that described above by using anti-NCA instead of anti-CEA.

What is claimed is:

1. In a process for producing monoclonal antibodies specific to a carcinoembryonic antigen by immunizing a first mammal with a first carcinoembryonic antigen to produce cells capable of producing antibodies, collecting the cells from the first mammal, fusing the collected cells with the cells of a line of myeloma of a second mammal, subjecting the thus-obtained fused cells to cloning, and culturing the thus-obtained hybridomas and recovering the desired monoclonal antibodies from the resulting spent culture, the improvement which comprises: selecting said fused cells by using the first carcinoembryonic antigen as a first marker on the basis of its capacity to produce antibodies reactive thereto and wherein said recovering step includes using at least one carcinoembryonic antigen other than said first carcinoembryonic antigen, normal faecal antigen-1, normal faecal antigen-2 and non-specific cross-reacting antigen of normal adult human faecal origin as a second marker for said hybridomas on the basis of the reactivities of hybridomas antibodies produced by said first monoclones with said second marker antigen(s).

2. A process as claimed in claim 1 wherein said recovering step includes using as said second marker at least two antigens selected from the group consisting of carcinoembryonic antigens other than the said first carcinoembryonic antigen, normal faecal antigen-1, normal faecal antigen-2 and non-specific cross-reacting antigen of normal adult human faecal origin.

3. A process according to claim 1 in which at least one of said first and second mammals is selected from the group consisting of mice, rats, guinea pigs, rabbits, goats, horses and cattle.

4. A process according to claim 1 in which said selecting is effected by radioimmunoassay using marker antigen labelled with a radioactive substance.

5. A monoclonal antibody produced by a process of claim 1.

6. A monoclonal antibody according to claim 5, which is reactive with a first carcinoembryonic antigen and unreactive with other antigens selected from the group consisting of carcinoembryonic antigens other than the first carcinoembryonic antigen, normal faecal antigen-1, normal faecal antigen-2 and non-specific cross-reacting antigen of normal adult human faecal origin.

7. A monoclonal antibody according to claim 5, which is reactive with at least two carcinoembryonic antigens and unreactive with at least one antigen selected from the group consisting of normal faecal antigen-1, normal faecal antigen-2 and non-specific cross-reacting antigen of normal adult human faecal origin.

8. A monoclonal antibody according to claim 5, which is reactive with at least two carcinoembryonic antigens, and with normal faecal antigen-1 and normal faecal antigen-2 of normal adult human faecal origin and unreactive with non-specific cross-reacting antigen of normal adult human faecal origin.

9. A monoclonal antibody according to claim 5, which is reactive with at least two carcinoembryonic antigens and with normal faecal antigen-2 of normal adult human faecal origin and unreactive with normal faecal antigen-1 and non-specific cross-reacting antigen of normal adult human faecal origin.

10. A monoclonal antibody according to claim 5, which is reactive with at least two carcinoembryonic antigens, normal faecal antigen-2 and non-specific cross-reacting antigen or normal adult human faecal origin and unreactive with normal faecal antigen-1 of normal adult human faecal origin.

11. A monoclonal antibody according to claim 5 in the form of an antiserum.

12. A process for determining the concentration of carcinoembryonic antigens and related antigens originating from the normal adult humans by radioimmunoassay, which comprises using a monoclonal antibody as defined in claim 5 as a marker antibody labelled with a radioactive substance.

* * * * *